US005719189A

United States Patent [19]
Schmidt et al.

[11] Patent Number: 5,719,189
[45] Date of Patent: Feb. 17, 1998

[54] MEDICINAL FEED FOR THE SYSTEMIC TREATMENT OF ECTOPARASITIC AND ECTOBACTERIAL DISEASES OF FISH

[75] Inventors: Hartmut Schmidt, Georgsmarienhütte; Günter Ritter, Bünde, both of Germany

[73] Assignee: Tetra Werke Dr. rer. nat. U. Baensch GmbH, Herrenteich, Germany

[21] Appl. No.: 287,754

[22] Filed: Aug. 9, 1994

Related U.S. Application Data

[62] Division of Ser. No. 949,324, Sep. 22, 1992, Pat. No. 5,618,847, which is a continuation of Ser. No. 709,867, Jun. 4, 1991, abandoned.

[30] Foreign Application Priority Data

Jun. 5, 1990 [DE] Germany .................. 40 17 964.8

[51] Int. Cl.$^6$ .................. A61K 31/135; A61K 31/16; A61K 31/045; A61K 31/17
[52] U.S. Cl. .................. 514/649; 514/629; 514/730; 514/588
[58] Field of Search .................. 514/730, 588, 514/629, 649

[56] References Cited

U.S. PATENT DOCUMENTS 4,225,588   9/1980   Gregg et al. .................. 424/177

OTHER PUBLICATIONS

"Nutrient Requirements of Warmwater Fishes and Shellfishes," 1983, National Academy Press, Chapter 5, pp. 48–81.

Handbook of Drugs and Chemicals Used in the Treatment of Fish Diseases, N. Herwig, 1979, pp. 128 and 136.

*Das Aquarium*, 220, Oct. 1987, L. Zenner, "Aus der praxis fur die Praxis", pp. 515, with explanation.

*Textbook of Fish Diseases*, E. Amlacher, pp. 53–66, 73–76, 157–162, and 179–206.

*Primary Examiner*—Theodore J. Criares
*Attorney, Agent, or Firm*—Elizabeth M. Anderson

[57] ABSTRACT

The present invention provides a medicinal feed for fish, which comprises a triphenylmethane derivative or a combination of triphenylmethane derivatives alone or in combination with at least one compound selected from the group consisting of thionine, nitrothiazole, nitrofuran, quinoline and acridine derivatives, compounds splitting off aldehydes, transition metal derivatives, metal colloids, hexamethylenetetramine and/or quaternary ammonium salts as active materials.

3 Claims, No Drawings

MEDICINAL FEED FOR THE SYSTEMIC TREATMENT OF ECTOPARASITIC AND ECTOBACTERIAL DISEASES OF FISH

This is a Divisional application of U.S. Ser. No. 07/949,324 filed Sep. 22, 1992 now U.S. Pat. No. 5,618,847, which is a Continuation application of U.S. Ser. No. 07/709,867, filed Jun. 4, 1991, now abandoned.

BACKGROUND OF THE INVENTION

The present invention is concerned with a medicinal feed for the systemic treatment of parasites in fish.

The care, breeding, and maintenance of fresh water and marine fish in hobby aquaria, in ponds and, to an even greater extent, in intensive maintenance installations of fish farming and aquaculture, are threatened by parasitic diseases which can endanger the fish and result in considerable financial losses. The following organisms pathological to fish occur especially frequently: dinoflagellates: *Oodinium pillularis* (fresh water) and *Oodinium ocellatum* (seawater); flagellates: *Costia necatrix* and *Hexamita symphysodonis*; ciliates: *Ichthyophthirius multifilis* (fresh water); monogenes: skin and gill flukes, for example Gyrodactylus and Dactylogyrus.

The treatment of ectoparasitoses, i.e., of diseases caused by parasites which live in or on the outer skin of fish, today occurs exclusively by the so-called bath therapy in which antiparasitic material is added to the maintenance water in appropriate biocidal concentrations.

Frequently, only the free-swimming parasitic stages, the so-called swarms, are thereby damaged but not the stages sitting securely in the skin or under the outer skin.

Consequently, the total treatment is based on the killing off of the swarms. There is no prevention of a new infection or reinfection or no effect on the immune system of the fish which additionally or exclusively combats the parasitic pathogenic stages.

According to the prevailing expert opinion, ectoparasitic diseases can only be treated externally and not be means of systemically administered curative agents, for example, medicinal feeds.

Endoparasitic diseases, for example, parasites of the gut, can be treated successfully almost exclusively by systemically administered curative agents, for example, medicinal feeds, such as are described in the literature (see N. Herwig, "Handbook of Drugs and Chemicals used in the Treatment of Fish Diseases", pp. 128 and 136, pub. Charles C. Thomas, Springfield, Ill., U.S.A.; E. Amlacher, "Taschenbuch der Fischkrankheiten", pub. Gustav Fischer Verlag, Stuttgart, 1981; L. Zemer, Das Aquarium, 220, 515/1987).

The bath therapy of ectoparasitic diseases of fish (fancy fish and useful fish) is frequently carried out with the use of biocidally or antiseptically acting dyestuffs, for example, of the triphenylmethane and acridine group of derivatives. These compounds include, for example, N-[4-[[4-(diethylamino)-phenyl]-phenylmethylene]-2,5-cyclohexadien-1-ylidene]-N-ethyl-ethanaminium sulfate (brilliant green); N-[4-[[4-(dimethylamino)-phenyl]-phenylmethylene]-2,5-cyclo-hexadien-1-ylidene]-N-methyl-methanaminium chloride and oxalate (malachite green); N-[4-[bis-[4-(dimethylamino)-phenyl]-methylene]-2,5-cyclohexadien-1-ylidene]-N-methylmethanaminium chloride (gentian violet); 3,6-diamino-10-methylacridinium chloride mixed with 3,6-dimainoacridine (acriflavine); 9-aminoacridine; and 2-ethoxy-6,9-diaminoacridinium lactate monohydrate (Rivanol).

In addition, active antiparasitic materials from other classes of chemical compounds are also used, for example, quinoline derivatives such as quinine; quaternary ammonium salts; silver and copper salts; metal colloids, nitrofurans, for example, nifurpirinol; and nitrothiazoles, for example, 2-amino-5-nitro-thiazole.

However, the bath therapy with these antiparasitic active materials involves several disadvantages. Parasites in or under the outer skin of the fish are mostly not affected. Since frequently the whole of the maintenance water (aquarium, pond, or intensive breeding installation) is treated, in addition, a very large use of active material is necessary.

Furthermore, the active material concentration is very uncertain since, during the treatment, due to decomposition processes (chemical, biological, and photochemical) and adsorption on surfaces, losses of active material occur which cannot be previously calculated. Since, to a large extent, the materials used are dyestuffs, the intensive coloration of the water and the tendency of the bath solution to color various materials is also disturbing. Since the whole of the maintenance system is therapeutically treated, the presence of the biocidally active materials leads to undesirable and, under certain circumstances, even harmful side effects, for example, damage to other important water organisms, such as aquatic plants and planktonic organisms and damage of the biological flora in filter systems and thus a negative influence on the biological breakdown capacity. The above-mentioned therapeutically active compounds also have a strong fish toxicity and especially gill toxicity so that the safety of the treatment is limited.

SUMMARY OF THE INVENTION

The present invention is a medicinal feed for fish containing a triphenylmethane derivative or a combination of triphenylmethane derivatives alone or in combination with one or more compounds selected from thionine, nitrothiazole, nitrofuran, quinoline and acridine derivatives, compounds splitting off aldehydes, transition metal derivatives, metal colloids, hexamethylenetetramine and/or quaternary ammonium salts as active ingredients and a pharmaceutically acceptable carrier.

The medicinal feed can be an enteral pharmaceutical composition containing an active ingredient in a concentration of from about 0.005 to about 10% by weight. Preferably it contains an active ingredient, or ingredients, in a concentration of from about 0.05 to about 3% by weight.

The medicinal feed can be a feed mixture.

Preferred active compounds are malachite green, a salt thereof or a derivative thereof; for example, malachite green chloride, malachite green carbinol base.

Other preferred active compounds are crystal violet, 9-aminoacridine, ethacridine lactate, acriflavine and methylene blue.

DETAILED DESCRIPTION

The present invention provides for the therapy of ectoparasitic and ectobacterial diseases in fish which avoid the above-mentioned disadvantages.

The present invention is a medicinal feed for fish containing a triphenylmethane derivative or a combination of triphenylmethane derivatives alone or in combination with at least one compound selected from the group comprising thionine, nitrothiazole, nitrofuran, quinoline and acridine derivatives, compounds splitting off aldehydes, transition metal derivatives, metal colloids, hexamethylenetetramine and/or quaternary ammonium salts as active materials.

The present invention is also concerned with the use of this medicinal feed for the systemic treatment of ectoparasitic and ectobacterial diseases. The medicinal feed according to the present invention preferably contains the active material in a concentration of from 0.005 to 10% by weight and more preferably of from 0.05 to 3% by weight.

The disadvantages of the bath therapy described above can be completely avoided by the use of the medicinal feed according to the present invention, which is completely surprising to the expert, for the systemic treatment of ectoparasitic and ectobacterial diseases of fancy and useful fish.

The effectiveness of systemically acting medicinal feeds against ectoparasites and ectobacteria, i.e., organisms which have attacked fish on and/or under the external skin and mucous membrane layer, is novel, surprising and not foreseeable by the expert. In comparison with the known bath therapy, the novel therapy of the present invention offers considerable advantages. Thus, for example, a precise, oral administration of the medicinal feed to the fish is possible. Parasites or bacteria in or under the outer skin of fish are, surprisingly, therapeutically attacked. The extraction of the active material from the medicinal feed by the maintenance water is very small. The amount of active material administered is very small, so the maintenance system has only negligible amounts of the active material. The toxic stressing of other water organisms is reduced practically to zero. The breakdown activity of the filter is not impaired. Coloration of the water is no longer recognizable. The gill toxic action is eliminated. Incalculable losses of active material during the treatment also no longer occurs.

A desired side effect is, at the same time, also the simultaneous combating of endoparasites possibly present.

The choice of appropriate active materials, with the novel medicinal feeds can also combat the following ectoparasites in the case of fancy and useful fish: (only the most important causal species are here given or have already been mentioned hereinbefore) dinoflagellates, such as Oodinium; flagellates, such as Costia (Hexamita); ciliates, such as Ichthyophthirius, Cryptocarion, Chilodonella and Trichodina; and Monogenea, such as skin and gill flukes, for example, Gyrodactylus and Dactylogyrus.

Surprisingly, ectobacterioses, for example, all skin and gill infections due to gram-negative and gram-positive bacteria, for example, Aeromonas, Pseudomonas, and Flexibacter, have also proved to be combatable.

In the systemic treatment of the ectoparasitoses and ectobacterioses, naturally at the same time, all systemic internal diseases of fancy and useful fish due to parasites and bacteria are treated when the active materials used have an appropriate spectrum of activity. This is a beneficial side effect.

Surprisingly, active materials which have previously either been used exclusively for bath therapy or, in exceptional cases, in the form of enteral pharmaceutical compositions exclusively for the treatment of internal parasitoses and preferably of gut parasitoses can be used for the systemic treatment of ectoparasitoses and ectobacterioses.

Triphenylmethane derivatives, for example, malachite green (as salts, for example chloride, oxalate and sulphate), malachite green carbinol base, brilliant green (all salts), crystal violet (all salts), gentian violet (all salts), pararosaniline (all salts, base), fuchsine (rosaniline) (all salts) as well as all leuco compounds of the cations of the dyes have been used exclusively for bath therapy. In addition, thionine derivatives, with the exception of methylene blue B; additional thionine derivatives with lower N-methylated derivatives as well as all leuco compounds of thionine derivatives; and nitrothiazole derivatives, for example, 2-amino-5-nitrothiazole and transition metal derivatives, for example copper and silver salts and complexes thereof, copper and silver metal colloids; and all microbicidal quaternary ammonium salts have been used.

Moreover some of the active compounds have been used in the mentioned pharmaceutical compositions for peroral treatment, but in no case for the treatment of ectoparasitic diseases, because this indication was not known. Compounds of this type are acridine derivatives, for example, acriflavine, 9-aminoacridine, atebrin, rivanol, and all reduced precursors of the acridine derivatives; methylene blue B; nitrofuran derivatives, for example, nifurpirinol; quinoline derivatives, for example, quinine (all salts, bases); aldehydes, for example, formaldehyde and derivatives thereof, for example, hexamethylenetetramine; enheptine and the N-acetyl derivative acimitrazole as well as trypaflavine and acriflavine.

Useful as a matrix or vehicle for the systemic use of the above-described anti-ectoparasitic and anti-ectobacterial active materials are: film-like feed, flock feed, pelletized feed, extruded feed, expanded feed, granulated feed, ground feed, pulverised feed, tableted feed, feed pastes and feed suspensions, feed gels and aspic feed or other carriers well enriched with attractants or baits.

The introduction of a therapeutically active material takes place in a technically appropriate preliminary stage of the production process, for example, into the raw material powder mixture and the water-containing process stages thereof in such a manner that distribution of the active material in a finished powder as fine and homogeneous as possible is achieved.

It has been found that most of the described active materials, especially when present in cationic form (for example, malachite green, acridinium salts, quaternary ammonium salts and the like), are very strongly adsorptively bound by the carrier or feed materials. The result of this outstanding active material immobilization is that no leaching out by water takes place and no discoloration, for example, on the hands of the user, results. In this way, a high degree of safety in the use of active materials which are toxic or dangerous to humans is achieved; thus no safety measures are necessary in the case of production, packaging, storage and in the case of therapeutic use.

Similar advantages are achieved by using reduced precursors of the cations of the dyes, e.g., leuco compounds, or other derivatives with poor solubility in water.

The following table summarizes, by way of example, the range of concentrations in the feed for some active materials. All the statements refer to mg/kg of active material of feed or to weights percent.

| Active Material | Concentration Range | | Preferred Concentration Range | |
|---|---|---|---|---|
| | mg/kg | % | mg/kg | % |
| Malachite Green Chloride (and Other Salts) | 100–10000 | 0.01–1.0 | 200–4000 | 0.02–0.4 |
| Malachite Green Carbinol Base | 100–10000 | 0.01–1.0 | 200–4000 | 0.02–0.4 |
| Crystal Violet | 100–10000 | 0.01–1.0 | 200–4000 | 0.02–0.4 |

-continued

| Active Material | Concentration Range | | Preferred Concentration Range | |
|---|---|---|---|---|
| | mg/kg | % | mg/kg | % |
| (Gentian Violet) | | | | |
| 9-aminoacridine | 100–50000 | 0.01–5.0 | 500–20000 | 0.05–2.0 |
| Ethacridine Lactate (Rivanol) | 200–50000 | 0.02–5.0 | 1000–30000 | 0.1–3.0 |
| Acriflavine (Trypaflavine) | 200–50000 | 0.02–5.0 | 500–30000 | 0.05–3.0 |
| Methylene Blue | 200–20000 | 0.02–2.0 | 500–10000 | 0.05–1.0 |

The medicinal feed variants of the present invention which can be used to treat ectoparasitoses and ectobasterioses have a beneficial side effect in that systemic diseases due to endoparasites and endobacteria in all types of fish of the fancy and the useful fish groups (fresh water and seawater) in all existing and in the usual closed and non-closed maintenance systems are also treated.

Even fish in their natural environment can be treated therapeutically by taking the feed.

A medicinal feed of the present invention is produced in the manner familiar to one skilled in the art in that either the desired active material is admixed with the raw feed mixture before the final working up to give flocks, pellets, tablets, capsules, extrudates or the like in the necessary amount or the final feed product is sprayed with a solution of the active material and subsequently finally dried.

The following examples are given for the purpose of further explaining the present invention without limiting the scope of the present invention:

EXAMPLE 1

A flock feed for fancy fish is enriched with 0.2% by weight of malachite green and given to ectoparasitically diseased fancy fish instead of the nonmedicated flock feed used for normal feeding.

A. Treatment of Ichthyophthirius 30 giant loach (*Botia macracautha*) and 30 thread fish (*Trichogaster trichopteri*) which were severely infected with Ichthyophthirius were fed once a day with the malachite green-containing medicinal feed. In comparison with the untreated control, within 5 days a 100% treatment success was achieved.

B. Treatment of Costia and Chilodonella 40 red neons (*Paracheirodon axelrodi*), which were double infected with Costia and Chilodonella, were fed once a day with malachite green-containing medicinal feed. In comparison with the untreated control, within 5 days a 100% treatment success was achieved.

C. Other Ectoparasitic Diseases

Analogous to the above-described Examples, with the described malachite green-containing medicinal feed, the following ectoparasitoses could be completely healed: *Oodinium pillulare, Trichodina spec.* and Gyrodactylus.

Corresponding healing successes are also achieved with the other medicinal feeds described hereinbefore.

Especially advantageous in the case of the treatment of ectoparasitoses with the instant medicinal feeds is their complete harmlessness: all the treated fish showed no signs of indisposition or of damage during and after the treatment.

Furthermore, the effectiveness of triphenylmethane dyestuffs, for example, brilliant green and malachite green, against gram-positive bacteria makes these active materials in the form of medicinal feeds according to the present invention of possible additional use for the treatment of external and internal bacterioses with gram-positive pathogens, for example, with Corynebacterium, Nocardia, and Mycobacterium.

The known effectiveness of crystal violet and gentian violet against internal worm diseases in humans and mammals can also be utilized for combating external and internal helminthoses in fish. Helminthoses which are brought about, for example, by Monogenea (for example, Gyrodactylus and Dactylogyrus), Cestoda, Trematoda (for example, Diplostomum) and Nematoda (for example, Capillaria) can be treated.

A further therapy lies in the combined use of the medicinal feed of the present invention and a healing agent bath in which similar or other antiparasitic or antibacterial active materials have been added to the water in a therapeutically effective amount. This combination therapy offers the possibility also of combating the nonparasitizing, free-swimming or firmly fixed (to plants, stones, or any surfaces) pathological stages. Advantages resulting therefrom are a partial or complete disinfection of the system, a reduction of the reinfection rate of the fish by free-swimming pathogenic stages, as well as combating of parasitizing pathogens on fish internally by the medicinal feed and externally by the healing bath.

In the case of the additional administration of the active material via the water, all the initially mentioned disadvantages of a bath therapy will arise.

We claim:

1. An enteral solid medicinal food preparation for fish, containing an active compound, a triphenylmethane, in a concentration of 0.005 to 10% by weight wherein the active compound is very strongly adsorptively bound by carriers and feed materials so no leaching out by water takes place.

2. A composition according to claim 1, containing an active compound in a concentration of 0.05 to 3% by weight.

3. A composition according to claim 1 which is a feed mixture.

* * * * *